United States Patent [19]

Pantoliano et al.

[11] Patent Number: 5,260,207
[45] Date of Patent: Nov. 9, 1993

[54] ENGINEERING OF ELECTROSTATIC INTERACTIONS AT METAL ION BINDING SITES FOR THE STABILIZATION OF PROTEINS

[75] Inventors: Michael W. Pantoliano, Germantown, Md.; Barry C. Finzel, Kalamazoo, Mich.; Philip N. Bryan, Silver Spring, Md.

[73] Assignee: Enzon Labs Inc., Gaithersburg, Md.

[21] Appl. No.: 600,179

[22] Filed: Oct. 19, 1990

Related U.S. Application Data

[63] Continuation of Ser. No. 178,168, Apr. 6, 1988, which is a continuation-in-part of Ser. No. 34,965, Apr. 6, 1987, abandoned.

[51] Int. Cl.$^5$ .......................... C12N 9/54; C12N 9/56; C11D 9/40
[52] U.S. Cl. .................... 435/221; 435/222; 252/174.12
[58] Field of Search .............. 435/221, 172.3, 222; 530/400; 252/174.12

[56] References Cited

U.S. PATENT DOCUMENTS 4,760,025 7/1988 Estell et al. .................. 435/222
4,914,031 4/1990 Zukowski et al. ............. 435/222

OTHER PUBLICATIONS

Voordouw, G. et al., *Biochemistry* 15:3716-3724 (1976).
Serpersu, E. H. et al., *Biochemistry* 26:1289-1300 (1987).
Tsuji, F. I. et al., *Proc. Natl. Acad. Sci. USA* 83:8107-8111 (1986).
Matthew, J. B., *Ann. Rev. Biophys. Chem.* 14:387-417 (1985).
Russell, S. T. et al., *J. Mol. Biol.* 185:389-404 (1985).
Bryan, P. et al., *Proc. Natl. Acad. Sci. USA* 83:3743-3745 (1986).
Drenth, J. et al., *Eur. J. Birchem.* 26:177-181 (1972).
Stuart, D. I. et al., *Nature* 324:84-87 (1986).
Holguin, J. A., *Arch. Biochem. Biophys.* 251:9-16 (1986).
Thomas, P. G. et al., *Nature* 318:375-376 (1985).
Estell, D. A. et al., *J. Biol. Chem.* 260: 6518-6521 (1985).
Liao, H. et al., *Proc. Natl. Acad. Sci. USA* 83:576-580 (1986).
Estell, D. A. et al., *World Biotech. Rep.* 2:181-187 (1984).
Pantoliano, M. W. et al., *Biochemistry* 26:2077-2082 (1987).
Bryan, P. N. et al., *Proteins: Structure, Function & Genetics* 1:326-334 (1986).
Cunningham, B. C. et al., *Protein Engineering* 1:319-325 (1987).
Vasantha, N. et al., *Genet. Biotechnol. Bacilli* 2:163-172 (1983).
Wells, J. A. et al., *Genet. Biotechnol. Bacilli* 2:173-180 (1983).
Shortle, D. et al., *Proc. Natl. Acad. Sci. USA* 75:2170-2174 (1978).
Vasantha, N. et al., *J. Bacteriol.* 159:811-819 (1984).
Jacobs, M. et al., *Nucl. Acids Res.* 13:8913-8926 (1985).
Nedkov, P. et al., *Biol. Chem. Hoppe-Syler* 366:421-430 (1985).
Kurihara, M. et al., *J. Biol. Chem.* 247:5619-5631 (1972).
Svendsen, I. et al., *FEBS Letts.* 196:228-232 (1986).
Meloun, B. et al. *FEBS Lett.* 183:195-200 (1985).
Jany, K.-D. et al., *Biol. Chem. Hoppe-Seyler* 366:485-492 (1985).
McPhalen, C. A. et al., *FEBS Lett.* 188:55-58 (1985).
Phaler, A. et al., *EMBO J.* 3:1311-1314 (1984).
Myers, R. M. et al., *Science* 229:242-247 (1985).
Folk, W. R. et al., *Cell* 33:585-593 (1983).
Wells, J. A. et al., *Nucl. Acids Res.* 11:7911-7925 (1983).
Smith, E. J., et al., (1968) J. Biol. Chem. 243, 2184-2191.
Gutteridge, S., et al. (1984) Embo J. 3(12), 2737-2743.

*Primary Examiner*—Charles L. Patterson, Jr.
*Attorney, Agent, or Firm*—Sterne, Kessler, Goldstein & Fox

[57] ABSTRACT

The present invention provides a method for redesigning proteins to increase the stability of the protein by altering amino acid residue(s) that are in close proximity to the protein's metal ion binding site(s). Further, the invention is directed to proteins that have been redesigned to have enhanced stability according to the methods of this invention.

11 Claims, 5 Drawing Sheets

ENGINEERING OF ELECTROSTATIC INTERACTIONS AT METAL ION BINDING SITES FOR THE STABILIZATION OF PROTEINS

This is a continuation of application Ser. No. 07/178,168, filed Apr. 6, 1988, which is a continuation-in-part of application Ser. No. 07/034,965, filed Apr. 6, 1987, now abandoned, the contents of which are fully incorporated herein by reference.

FIELD OF THE INVENTION

The present invention relates to designing proteins with enhanced stability through the alteration of the proteins' divalent metal ion binding sites.

BACKGROUND OF THE INVENTION

Proteins are linear polymers of amino acids. Since the polymerization reaction which produces a protein results in the loss of one molecule of water from each amino acid, proteins are often said to be composed of amino acid "residues." Natural protein molecules may contain as many as 20 different types of amino acid residues, each of which contains a distinctive side chain. The sequence of amino acids in a protein defines the primary structure of the protein.

Proteins fold into a three-dimensional structure. The folding is determined by the sequence of amino acids and by the protein's environment. The remarkable properties of proteins depend directly from the protein's three-dimensional conformation. Thus, this conformation determines the activity or stability of enzymes, the capacity and specificity of binding proteins, and the structural attributes of receptor molecules. Because the three-dimensional structure of a protein molecule is so significant, it has long been recognized that a means for stabilizing a protein's three-dimensional structure would be highly desirable.

The three-dimensional structure of a protein may be determined in a number of ways. Perhaps the best known way of determining protein structure involves the use of the technique of X-ray crystallography. An excellent general review of this technique can be found in *Physical Bio-chemistry*, Van Holde, K. E. (Prentice-Hall, N.J. (1971) pp221–239) which reference is herein incorporated by reference. Using this technique, it is possible to elucidate three-dimensional structure with remarkable precision. It is also possible to probe the three-dimensional structure of a protein using circular dichroism, light scattering, or by measuring the absorption and emission of radiant energy (Van Holde, *Physical Biochemistry*, Prentice-Hall, N.J. (1971)). Additionally, protein structure may be determined through the use of the techniques of neutron defraction, or by nuclear magnetic resonance (*Physical Chemistry*, 4th Ed. Moore, W. J., Prentice-Hall, N.J. (1972) which reference is hereby incorporated by reference).

The examination of the three-dimensional structure of numerous natural proteins has revealed a number of recurring patterns. Alpha helices, parallel beta sheets, and anti-parallel beta sheets are the most common patterns observed. An excellent description of such protein patterns is provided by Dickerson, R. E., et al. In: *The Structure and Action of Proteins*, W. A. Benjamin, Inc., Calif. (1969). The assignment of each amino acid to one of these patterns defines the secondary structure of the protein. The helices, sheets and turns of a protein's secondary structure pack together to produce the three-dimensional structure of the protein. The three-dimensional structure of many proteins may be characterized as having internal surfaces (directed away from the aqueous environment in which the protein is normally found) and external surfaces (which are in close proximity to the aqueous environment). Through the study of many natural proteins, researchers have discovered that hydrophobic residues (such as tryptophan, phenylalanine, tyrosine, leucine, isoleucine, valine, or methionine) are most frequently found on the internal surface of protein molecules. In contrast, hydrophilic residues (such as asparate, asparagine, glutamate, glutamine, lysine, arginine, histidine, serine, threonine, glycine, and proline) are most frequently found on the external protein surface. The amino acids alanine, glycine, serine and threonine are encountered with equal frequency on both the internal and external protein surfaces.

Proteins exist in a dynamic equilibrium between a folded, ordered state and an unfolded, disordered state. This equilibrium in part reflects the short range interactions between the different segments of the polypeptide chain which tend to stabilize the protein's structure, and, on the other hand, those thermodynamic forces which tend to promote the randomization of the molecule.

Metal ions have long been known to stabilize proteins by binding at specific sites in the tertiary structure. Indeed, many proteins isolated from thermophilic organisms have been shown to contain calcium ion binding sites. These sites are responsible for the enhanced stability that these proteins require in order to function in the elevated temperature milieu in which they are found. For example, thermolysin, a neutral protease from the thermophilic organism *Bacillus thermoproteolytichs*, was found to contain four calcium binding sites. By studying the calcium ion dependence for the rate of thermal inactivation, it has been possible to estimate the collective contribution of these sites to the G of unfolding to be between 8.1 and 9.2 Kcal/mole (Vorrdouw et al., *Biochemistry* 15:3716–3724 (1976)).

For example, Serpersu et al., *Biochemistry* 26:1289–1300 (1987) replaced the carboxylate ligand of residue aspartic acid 40 in the calcium binding site of staphylococcal nuclease with a glycine resulting in a 7.4 fold decrease in affinity for calcium ions. Similarly, Tsuju et al., *Proc. Nat'l Acad. Sci. USA*, 83:8107–8111 (1986) changed glycines in the vicinity of the calcium binding loops in the photoprotein aequorin to positively charged arginines to cause a decrease in the affinity of metal binding at these sites. It would, however, be desirable to design proteins with increased stability by increasing the binding affinity of divalent metal cations at a specific site in the protein through specific amino acid substitutions.

SUMMARY OF THE INVENTION

The present invention provides a method for redesigning proteins to increase the stability of the protein by altering amino acid residue(s) that are in close proximity to the protein's metal ion binding site(s). In detail, the method of this invention involves the following steps:

1. Correlating the metal ion binding structural site with some parameter of protein stability; and
2. Altering the metal ion binding site through the substitution, insertion, or deletion of amino acid residues in close proximity to that site so that the electrostatic attraction interaction between the amino acids and the metal ion is increased.

In identifying the metal ion binding site for correlation with a parameter of protein stability, one may analyze the three dimensional structure of a protein of interest or some evolutionarily related variant. The three dimensional structure may be obtained from published sources, or determined by known methods of X-ray crystallography.

In altering the metal ion binding site through the substitution, insertion, or deletion, of amino acid residues, the following steps are considered in the method of this invention:

(a) Selecting amino acids for substitution, insertion, or deletion as close as possible to the metal ion binding site, but without introducing steric hindrance;

(b) Preferentially selecting for substitution, insertion, or deletion those amino acids that are not conserved in evolutionally related homologous proteins;

(c) Changing positively charged amino acid residues that are close to the bound metal ion to uncharged or negatively charged amino acid residues; and (d) Preferentially using computer-assisted graphics to simulate the introduction of the new amino acid residues.

Further, the invention is directed to proteins that have been redesigned to have enhanced stability according to the methods of this invention.

DEFINITIONS

The following definitions are used in describing the invention.

Protein

A heteropolymer made by living cells and composed of amino acids. A typical protein comprises 100 to 1000 amino acids. The exact sequence of amino acids determines the structure and function of the protein.

Amino acid

One of the twenty naturally occurring compounds which are the building blocks of proteins. The natural amino acids are usually abbreviated to either three letters or one letter according to Table 1. The amino acids are joined head to tail to form a long main chain. Each kind of amino acid has a different side group.

TABLE 1

| Amino acid names and abbreviations. | | |
|---|---|---|
| Amino Acid | Three letter code | Single letter code |
| Alanine | Ala | A |
| Arginine | Arg | R |
| Aspartic acid | Asp | D |
| Aparagine | Asn | N |
| Cysteine | Cys | C |
| Glutamic acid | Gly | E |
| Glutamine | Gln | Q |
| Glycine | Gly | G |
| Histidine | His | H |
| Isoleucine | Ile | I |
| Leucine | Leu | L |
| Methionine | Met | M |
| Phenylalanine | Phe | F |
| Proline | Pro | P |
| Serine | Ser | S |
| Threonine | Thr | T |
| Tryptophane | Trp | W |
| Tyrosine | Tyr | Y |
| Valine | Val | V |

Atom names

All amino acids have the same atoms in the main chain and differ only in the side chains. The main-chain atoms are a nitrogen, two carbons, and one oxygen. The first atom is the nitrogen, called simply N. The next atom is a carbon and is called the alpha-carbon. Side groups are attached to this alpha-carbon. The alpha-carbon is connected to the carbonyl carbon which is called C. C is connected to the carbonyl oxygen (called O) and to the N of the next residue. The side group atoms are given names composed of the symbol for the element (C, O, N, S), a Greek letter (alpha, beta, gamma, delta, epsilon, zeta and eta), and perhaps an arabic numeral if the side group is forked.

Free energy

A thermodynamic quantity which describes the behavior of systems in dynamic equilibrium. The symbol G represents the Gibbs free energy.

Electrostatic attractive interaction

The electrostatic attractive interaction is defined in terms of Coulomb's law:

$$\Delta E = Z_a Z_b e^2 / D^{eff} r_{ab}$$

where $\Delta E$ is the energy change that results from bringing two charges, a and b initially separated by infinity, to some distance, $r_{ab}$. $Z_a$ and $Z_b$ are the respective number of unit charges; e is one unit of charge. When the charges a and b are of opposite signs, the coulombic interaction is attractive. When the positive charge is a divalent metal ion, and the negative charges come from an array of points in the structure of a protein, then the same energy involved in this attractive interaction must be overcome in order to unfold the protein. This means that the free energy of metal ion binding is added to the overall free energy change for unfolding, $\Delta G_u$, thus making this latter parameter more positive and shifting the equilibrium to the folded state.

Metal ion binding site

A structural segment or segments of polypeptide chain folded in such a way so as to give the proper geometry and electrostatic configuration for binding a divalent metal ion. This is the physical arrangement of protein atoms around a bound metal ion.

Protein stability

Protein is defined herein in terms of the $\Delta G$ of unfolding. The larger $\Delta G$ the more the equilibrium folded $\rightleftarrows$ unfolded is shifted in favor of the folded state. One can get an estimate of $\Delta G_u$ from the midpoint of the unfolding transition, Tm, measured by scanning calorimetry. Alternatively one may measure the kinetic stability of a protein from the rate of thermal inactivation.

DETAILED DESCRIPTION OF THE INVENTION

This invention is directed to methods for the redesign of the tertiary structure of proteins in order to increase the stability of their correctly folded and biologically and/or catalytically active state. The methods of this invention demonstrate how to increase the electrostatic interactions between proteins and divalent metal cations in order to increase the binding constant for metal ion binding. The increased electrostatic attraction between the protein and metal ion as measured by an increase in the free energy of dissociation, $\Delta G_{el}$, directly translates into an increase in the free energy of unfolding, $\Delta G_u$, for the protein of interest, thereby yielding enhanced stability for the folded protein structure.

The guide for designing the alteration of the metal ion binding site through the substitution, deletion, or insertion of amino acid residues is Coulomb's law:

$$\Delta E = Z_a Z_b e^2 / D^{eff} r_{ab} \quad \text{(equation 1)}$$

where $\Delta E$, measured in Kcal/mole, is the change in energy for a system that consists of two point charges, a and b, as they are brought together as a function of their distance of separation, $r_{ab}$. $Z_a$ and $Z_b$ are the respective number of unit charges; e is one unit of electronic charge ($4.8032 \times 10^{-10}$ esu); and D is the dielectric constant. In the case of a divalent metal cation binding site, $Z_a = 2+$. If $Z_b$ is a charge of the opposite sign then the interaction is attractive and the energy of the system is decreased. But if the sign of $Z_b$ is positive then the interaction becomes repulsive and the energy of the system is increased. It should be noted that for natural systems like proteins, where the charges are not point charges, there is a limit to how small $r_{ab}$ can become before steric problems result. The lower limit of $r_{ab}$ therefore has been found to be in the range of 2 to 3 Å for low molecular weight ion complexes.

The special case where the electrostatic interaction is between a metal ion and negatively charged or dipolar ligands has been thoroughly studied and understood through the use of the electrostatic crystal field theory (CFT) first expounded by H. Bethe in 1929. This theory treats the interaction between the metal ion and the ligands as a purely electrostatic problem in which the ligands are treated as point charges (or point dipoles). This theory did not adequately explain the covalent nature of some metal-ligand interactions and has been modified into the adjusted crystal field theory (ACFT) or the ligand field theory (LFT) in order to allow for covalency (Cotton & Wilkinson, *Advanced Inorganic Chemistry*, Interscience, John Wiley pub., N.Y. 3d ed. (1972)). However, in the cases where the divalent metal ion in question is from the Group II metals, i.e., $Mg^{2+}$, $Ca^{2+}$, $Sr^{2+}$, and $Ba^{2+}$, then the CFT does quite well in predicting geometry, affinity ($K_d$), and other physical chemical parameters of these metal ion complexes. The reason for the CFT success in these cases is due to the fact that the d electron orbitals responsible for the covalency of transition metal ion complexes are empty for the Group II divalent metal ions, thereby greatly simplifying the correlation of experimental results with theory.

One major source of uncertainty that is encountered in electrostatic interactions in proteins is the dielectric constant. It varies non-uniformly depending on shielding and charge effects. Many attempts have been made to simulate the effective screening (dielectric value) of electrostatic charges inside the tertiary structures of folded proteins (Matthew, *Ann. Rev. Biophys. Chem.*, 14:387–417 (1985)). Even the most sophisticated models, however, have a 5 kcal/mole error range (more than 3 pKa units) when attempting to calculate intrinsic pKa values of ionizable groups inside proteins (Russell & Warshel, *J. Mol. Biol.*, 185:389–404 (1985)). Nevertheless, electrostatic interactions are expected to be significant over relatively long distances even with moderate screening, and vary inversely with the linear distance.

The electrostatic forces described above are also involved in interactions between uncharged but polar molecules, but the energy of the interaction is more complex than that between simple ions. The energy expression for such interactions also generally varies inversely with the distance between such molecules, raised to a power usually greater than 1 but less than 6 (Creighton, *Proteins: Structure and Molecular Properties*, Freeman & Co., N.Y. (1984)). This is due to the polarizability of dipoles when in the vicinity of electric fields, i.e., Group II metals, $M^{2+}$. It is thus easier to predict results with charged ions. For these reasons, it is preferred to use Group II metals, $M^{2+}$, in this invention and charged side groups of amino acids residues; $COO^-$ of Asp and Glu; $NH^{3+}$ of Lys and the amino-terminus, and the guanidinium cationic group of Arg.

According to the methods of this invention, a metal ion binding site in a protein can be enhanced to increase the affinity for divalent metal ions. In general, the methods of this invention comprise the following steps:

A.) Correlating the metal ion binding structural site with some parameter of protein stability—This parameter can be the rate of thermal inactivation derived from kinetic experiments at elevated temperatures and varying concentrations of metal ion. Alternatively, one may use thermodynamic measurements of the melting temperature, Tm, derived from calorimetry or some other physical assessment of the unfolding transition. These measurements not only allow an estimate of the degree to which one is successful in affecting stability in a desirable way but also allow an estimate of the affinity of this site for divalent metal ions.

In identifying the metal ion binding site for correlation with a parameter of protein stability one may analyze the three dimensional structure of the protein of interest or some evolutionarily related variant. The three-dimensional structure may be obtained from published sources or determined by known methods of X-ray crystallography. Other methods of obtaining structural information may include circular dichroism, light scattering, measuring the absorption and emission of radiant energy, neutron diffraction, and magnetic resonance.

B.) Altering the metal ion binding site through the substitution, insertion, or deletion of amino acid residue(s) in close proximity to that site so that the electrostatic attractive interaction between the amino acids and the metal ion is increased—These amino acid changes may be introduced into the cloned, sequenced gene for the protein by the technique of oligonucleotide site-directed in vitro mutagenesis. This method is described in detail in Bryan et al., *Proc. Nat'l Acad. Sci. USA* 83:3743-3745 (1986), incorporated herein by reference.

The criteria for selection of amino acids in close proximity to the bound metal ion for substitution, insertion, or deletion via site-directed mutagenesis is as follows:

Select amino acids for substitution, insertion, or deletion as close as possible to the bound metal ion, but without introducing steric hinderance. Amino acids are selected for substitution, insertion, or deletion that will optimize the distance and geometry of the electrostatic attractive forces at the binding site.

(a) In substituting amino acids, preference should be given to changing those amino acids that are not conserved in evolutionarily related homologous proteins. Conserved amino acids in evolutionarily related homologous proteins will generally indicate that these conserved amino acids are favorable to the protein and should be maintained. In contradistinction, amino acid substitutions should be evaluated that differ (variable positions) in the area of the metal ion binding site between the protein to be altered and in evolutionarily related homologous proteins. Thus, for example, if the protein to be altered contains a neutral residue in the region of binding and a related protein contains an Asp or Glu (negatively charged), then high priority should be given to substituting the neutral residue with Asp or Glu.

(b) In insertion and/or deletion of amino acid residues, preference should be given to those amino acids that will optimize the distance and geometry of ligand interactions. In general, this involves creating a radius between the amino acid(s) and the metal ion as close as possible to 2.5Å that can be obtained without creating steric hindrance. For example, if a position when changed to Asp or Glu is not at the optimum distance (2.5Å) from the metal ion, then the introduction of an insertion or deletion in this vicinity may allow the Asp or Glu to swing in closer in distance to that found to be optimal.

(c) Positively charged residues that are close to the bound metal ion should be changed to neutral or negatively charged residues. Positively charged residues may also simply be deleted. Neutral or negatively charged residues may be inserted. Combinations of insertions, deletions, and substitutions are contemplated according to the methods of this invention. As the divalent metal ion has a positive charge, changing positively charged residues to neutral or negatively charged residues will increase the affinity of the metal ion binding site.

Candidate amino acid substitutions selected by the criteria given above may then be simulated on a high resolution computer graphics system such as the Evans Sutherland Model PS330 interfaced with a computer of suitable configuration such as the VAX 11/780. Such a graphics system allows one to graphically make the proposed change and test whether there are any obvious steric problems that the new amino acid residue will introduce, assuming there is no movement of the main chain atoms of the polypeptide fold. The criteria employed in such an analysis are as follows:

a) Measure the interatomic distances between most of the atoms of the proposed residue's side chain with those of most of the atoms of its nearest neighbors in the protein structure.

b) If there are any serious violations of the van der Waals radii of any of the atoms or severe electrostatic repulsion between any of the negative charges, then rotate one or more of the bonds in an attempt to reduce these effects. If either a) or b) gives a structure with no serious van der Waals radii violations or electrostatic repulsions, then introduce the proposed change into the protein via site-directed mutagenesis. If serious van der Waals radii violations or electrostatic repulsions persist, then give the change a low priority for experimental evaluation.

Proteins that may be redesigned according to the meth invention include those that have $M^{2+}$ metal binding sites. The majority of proteins with divalent metal ion binding sites are enzymes with calcium ion binding sites, although enzymes with other divalent metal ion binding sites are known. Selection of the proteins to be redesigned will depend, of course, on the ultimate contemplated use of the redesigned protein. Further, as used herein the use of the term protein is intended to also mean protein fragments, such as polypeptides.

The largest class of naturally occurring proteins is made up of enzymes. Each enzyme generally catalyzes a different kind of chemical reaction, and is usually highly specific in its function. Although there may be slight variations in a distinct type of naturally occurring enzyme within a given species of organism, enzymes of a specific type produced by organisms of the same species generally are substantially identical with respect to substrate specificity, thermal stability, activity levels under various conditions (e.g., temperature and pH), oxidation stability, and the like. Such characteristics of a naturally occurring or "wild-type" enzyme are not necessarily optimized for utilization outside of the natural environment of the enzyme. Thus, it may be desirable to alter a natural characteristic of an enzyme to optimize a certain property of the enzyme for a specific use, or for use in a specific environment according to this invention.

Preferably, the methods according to this invention are used to mutate serine proteases to enhance certain characteristics, particularly thermal stability. A protease is a catalyst for the cleavage of peptide bonds. A serine protease is an enzyme which has an essential serine residue at the active site and catalyzes the hydrolysis of peptide bonds. Serine proteases can be inhibited by phenylmethanesulfonylfluoride and by diisopropylfluorophosphate. A subtilisin is a serine protease produced by Gram positive bacteria or fungi. These serine proteases may include, but are not limited to, those from *Bacillus amyloliquefaciens*, subtilisin Carlsberg from *Bacillus licheniformis*, subtilisin DY from *Bacillus DY*, subtilisin amylosachariticus from *Bacillus amylosachariticus*, and mesentericopeptidase. Fungal proteases, such as protease K, thermomycolase, and thermitase from *Thermoactinomyces vulgaris* may also be enhanced in accordance with the invention, as well as mammalian proteases produced in a bacterial host.

Other preferred proteins to be redesigned according to the methods o this invention include those proteins having weak divalent metal ion binding sites. Examples of such proteins include alpha amylase, glucose isomerase, themolysin, and neutral protease. Generally in wild-type proteins, the divalent metal is calcium, although binding sites with other divalent metals are known. (Creighton, *Proteins: Structure and Molecular Properties*, Freeman & Co., N.Y. (1984)).

The amino acid substitutions, deletions, and insertions may be accomplished by site-directed (i.e., oligonucleotide) mutagenesis. Site-directed mutagenesis is well-known in the art and is described in detail in Bryan et al., *Proc. Nat'l Acad. Sci. USA* 83:3743–3745 (1986), incorporated herein by reference.

Further, in another embodiment of this invention, regional directed in vitro random mutagenesis is used to alter the amino acid residue(s) in the loops responsible for metal ion binding in the protein of interest. The preferred procedure for in vitro random mutagenesis is described in detail in U.S. patent application Ser. No. 828,545 and PCT application PCT/US87/00348, both incorporated herein by reference. The new variants generated by this procedure can be screened or selected for those variants that exhibit the desired parameter of enhanced protein stability. These screened or selected variants can then be further characterized first through genetic manipulations to identify the change(s) in amino acid residue(s). In addition, these screened or selected variants can be further identified by kinetic and thermodynamic characterization of stability. Finally, these variant proteins may be crystallized and X-ray crystal structures obtained at high resolution to fully correlate the increased stability with known protein structural information.

To further enhance the stability of these variant proteins, additional modifications to the amino acid residue(s) in close proximity to a metal ion binding site(s) may be effected according to the previously described methods of this invention.

In general, prior to mutation of a gene coding for an enzyme of interest, the gene generally is first isolated from its natural source and cloned in a cloning vector. Alternatively, mRNA which is transcribed from the gene of interest can be isolated from the source cell and converted into cDNA by reverse transcription for insertion into a cloning vector. A cloning vector can be a phage or plasmid, and generally includes a replicon for autonomous replication of the vector in a microorganism independent of the genome of the microorganism. A cloning vector advantageously includes one or more phenotypic markers, such as DNA coding for antibiotic resistance, to aid in selection of microorganisms transformed by the vector.

Procedures for insertion of DNA or cDNA into a vector for cloning purposes are well known in the art. These procedures generally include insertion of the gene of interest into an opened restriction endonuclease site in the vector, and may involve addition of polymeric tails of deoxynucleotides to the ends of the gene and linking the gene to opened ends of a cloning vector having complementary polymeric tails.

A gene of interest to be altered by site-directed mutagenesis can be present in an expression vector. An expression vector generally falls under the definition of a cloning vector since an expression vector usually includes the components of a typical cloning vector, namely one or more replicons as defined above, and one or more phenotypic markers for selection purposes. Additionally, an expression vector includes control sequences encoding a promoter, operator, ribosome binding site, and translation initiation signal. For expression under the direction of the control sequences, a target gene to be treated according to the invention is operably linked with the control sequences in the proper reading frame. An expression vector containing the DNA sequence to be targeted can be a phage or a plasmid, with plasmids being preferred.

Figure 4:
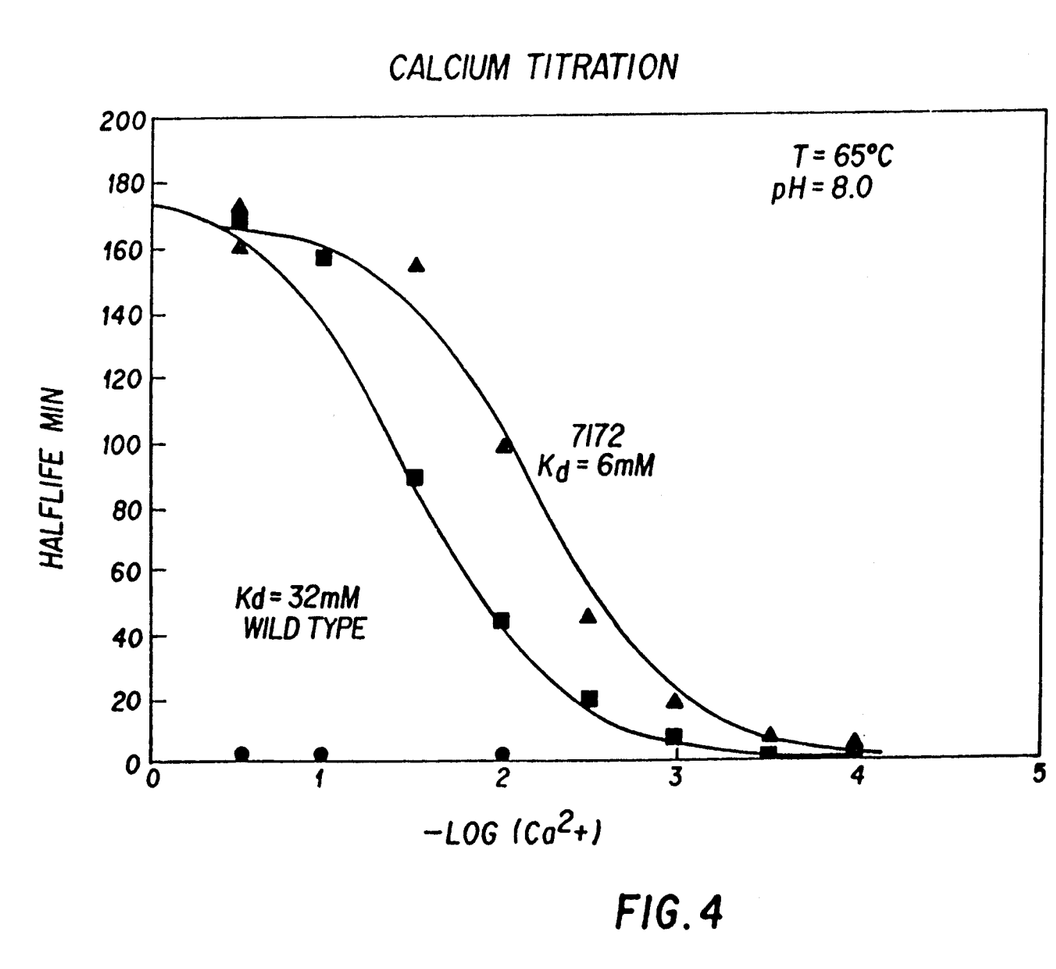
FIG. 4 shows calcium ion dependence for the rate of thermal inactivation of subtilisin at 65° C. The data for subtilisin 7172 is denoted by ( ) and for the wild-type subtilisin BPN' by ( ). The ( ) denotes the effect of MgCl₂ on the subtilisin BPN'. The solid lines represent theoretical titration curves for single metal ion binding sites having the affinity ($K_d$) shown.
Figure 5:
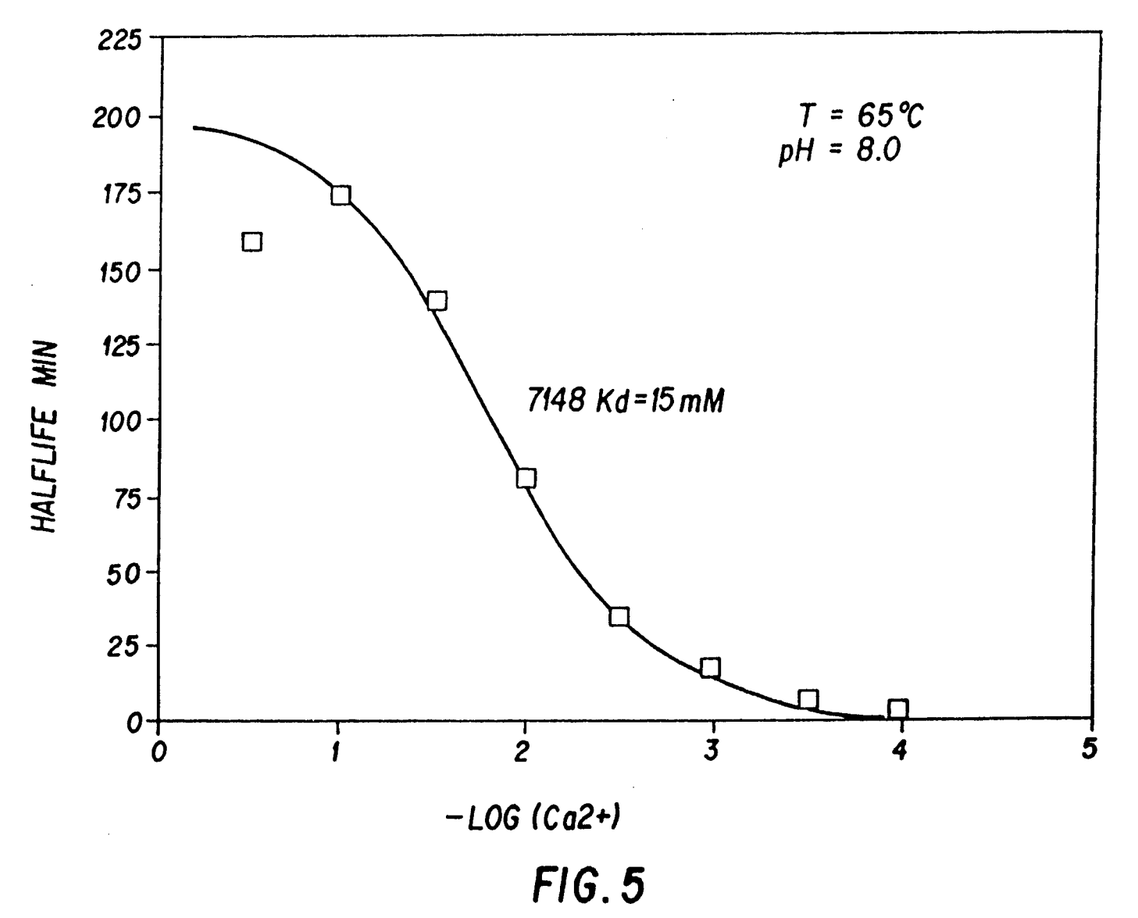
FIG. 5 shows calcium ion dependence for the rate of thermal inactivation of subtilisin 7148 at 65° C.

By using the methods of this invention, subtilisin 7172 with an amino acid substitution of Pro 172 to Asp has been created. As shown in FIG. 4, the new subtilisin 7172 has a five-fold increase in the affinity for calcium over wild-type subtilisin BPN'. Subtilisin 8312 was also created, with an amino acid substitution of Pro 172 to Glu. Subtilisin 8312 was found to be similar to subtilisin 7172. Subtilisin 7148 with a substitution of Gly 131 to Asp has also been created. FIG. 5 shows that new subtilisin 7148 has a two-fold increase in the affinity for calcium over the wild-type subtilisin BPN'. As discussed in the Examples, the difference in the binding strength is believed to be due to the distances between the substitutions and the binding site, in 7172 and 8312 it is 5Å and in 7148 it is 10Å away from the divalent metal cation.

This invention is intended to be useful for the stabilization of many different kinds of proteins under a variety of conditions. For example, microbial serine proteases are used as an active ingredient in detergent formulations for the enhancement of detergent performance. Subtilisin-like proteases are currently used in detergent formulations to improve the removal of protein stains such as blood and milk from soiled garments. These detergent formulations can often present conditions of pH, temperature, free metal ion concentrations, and detergent content (hydrophobicity) that do not favor the properly folded state of enzymes, i.e. subtilisin-like proteases. Therefore, the present invention provides subtilisin enzymes of enhanced stability that may be used in these applications.

In particular, subtilisin enzymes of this invention can be used as an additive to washing preparations, such as liquid detergents, especially citrate-based liquid detergents, which are used for cleaning fabric. The subtilisin enzymes of this invention are more thermally stable than wild-type subtilisin and thus does not lose activity as rapidly as wild-type when stored in solution with detergents or when subjected to high heat during use in cleaning. By use of the subtilisin enzymes of this invention as an additive in washing preparations, the removal of proteinaceous stains on fabric is improved. The amount of subtilisin enzyme that may be used as an additive to washing preparations are well-known in the art, or may readily be ascertained by routine experimentation. The optimal range of enzyme concentration will, of course, be related to the cost of the enzyme and the amount of cleaning needed. Typically, the amount of subtilisin enzyme added to a washing preparation will be from about 2000 to about 4000 Alkaline Delft Units/gram (ADU/gm) of washing preparation.

The following examples are presented to illustrate the invention and are not intended to be limiting.

EXAMPLE I

REDESIGN OF SUBTILISIN BPN'

Figure 1:
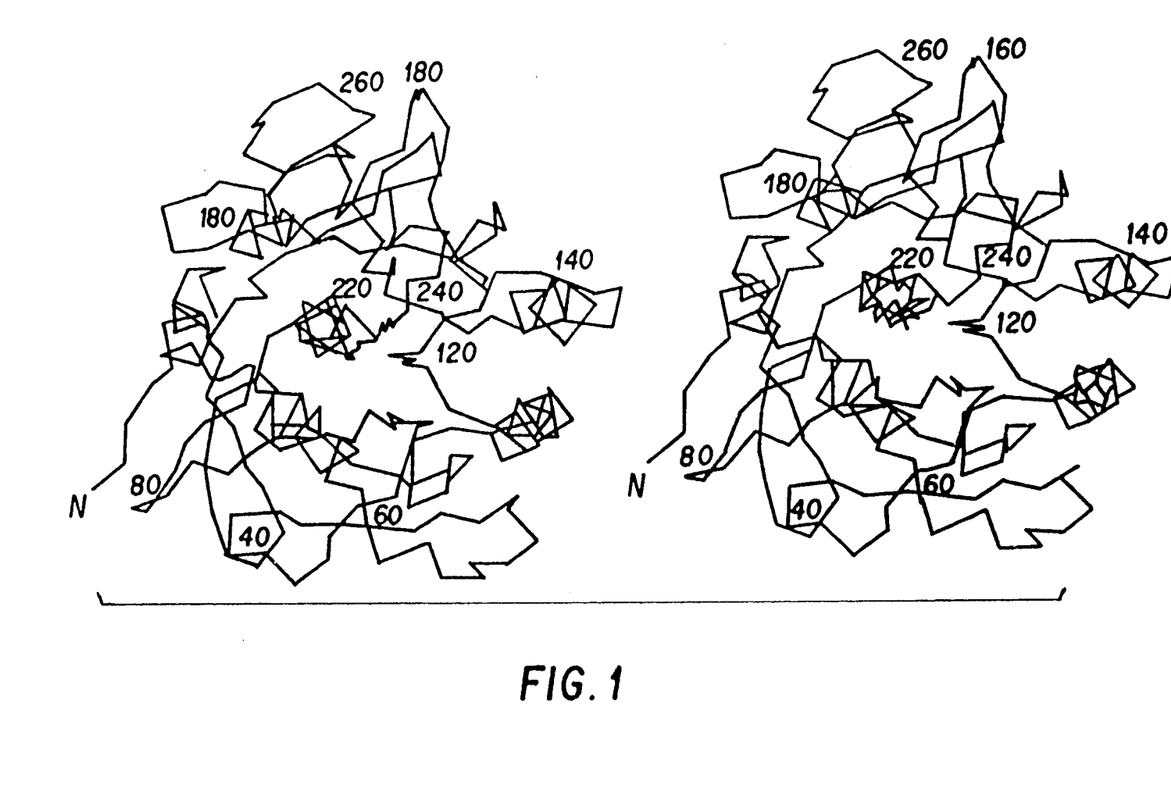
FIG. 1 shows a 1.3Å resolution X-ray structure of subtilisin BPN' in stereo. The two calcium binding sites are labeled CaA and CaB.
Figure 2:
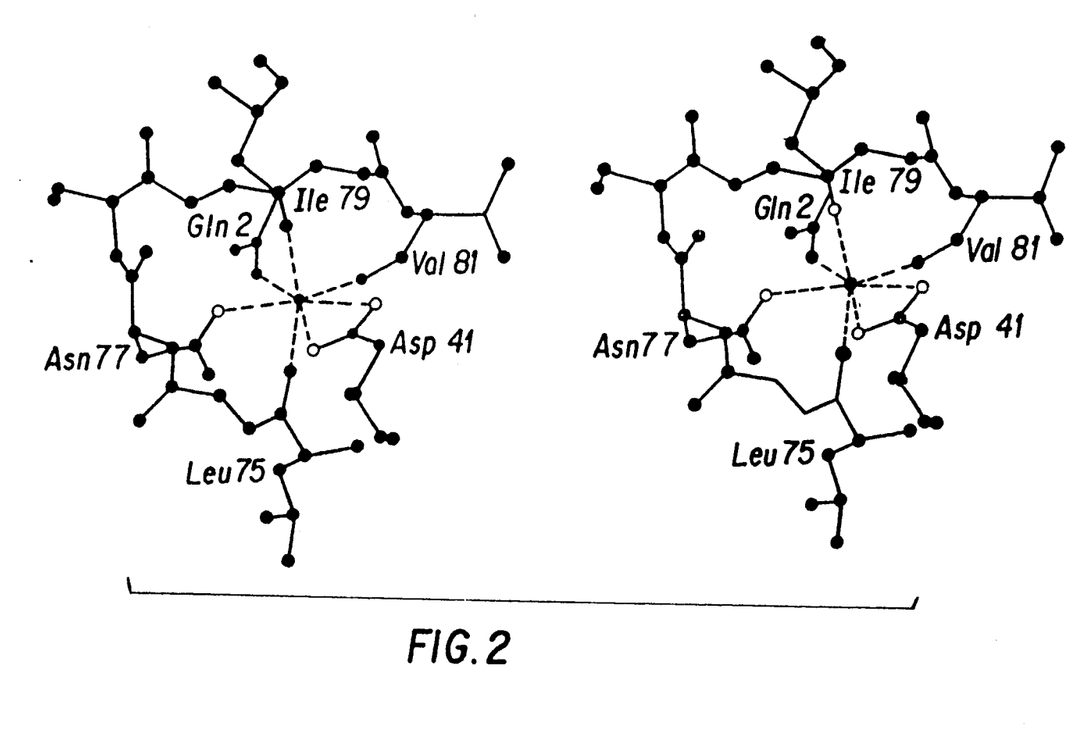
FIG. 2 shows detailed structural information for the calcium A (CaA) binding site in stereo.

An X-ray crystallographic structure of subtilisin BPN' at 1.3Å resolution is shown in FIG. 1. Two metal ion binding sites were found at opposite ends of the globular protein. One site is located near the NH$_2$-terminus and is labeled calcium site A since this site was found to preferentially bind calcium ions even in the presence of EDTA at 4° C. A more detailed view of this site is shown in FIG. 2. Seven protein-derived oxygen ligands are arranged about site A in an approximately octahedral geometry if one considers the two Asp 41 oxygen ligands as one site. Three of these ligands are main chain carbonyl oxygen atoms that originate from Ile 79, Val 81, and Leu 75. The other four originate from the side chain atoms of Asp 41, Gln 2, and Asn 77. All seven have an average oxygen-calcium distance of 2.4Å.

Figure 3:
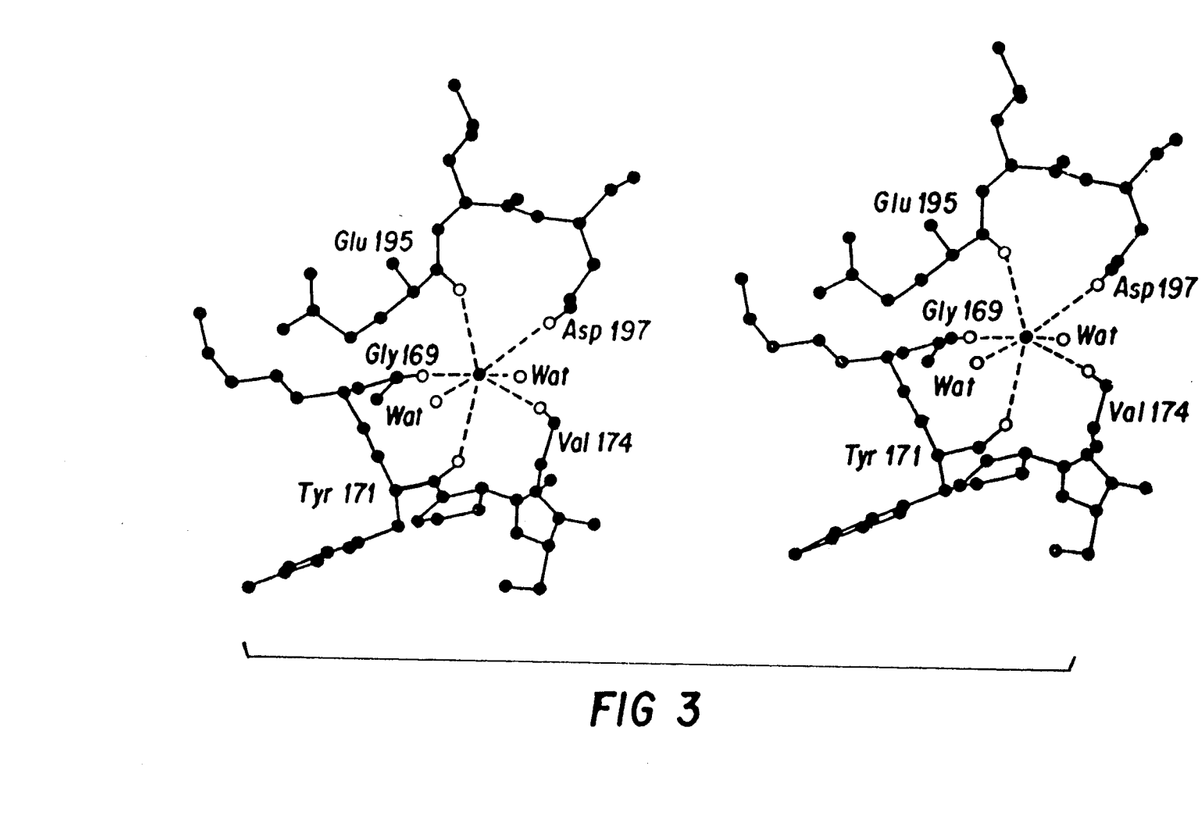
FIG. 3 shows detailed structural information for the calcium B (CaB) binding site in stereo.

The second metal binding site is labeled calcium site B and is located about 20Å from site A. The second site is located in a crevice defined by two segments of the polypeptide chain. The first segment contributes three main chain carbonyl oxygen atoms as ligands: Gly 169, Tyr 171, and Val 174 (see FIG. 3), and the second segment contributes an additional main chain oxygen atom (Glu 195) along with an oxygen atom derived from a side chain carboxylate group (Asp 197). Two water molecules round out the seven member coordination sphere. Because this site is located on the surface it is more exposed to solvent than is site A. The mean cation-oxygen ligand distance is also longer in site B (2.9Å vs. 2.4Å in site A). See Table II for actual calcium-ligand distances in the two sites.

TABLE II

Cation-Ligand* Distances from 1.3Å Resolution X-ray Model.

| Calcium Site A | | | Calcium-Site B | | |
| --- | --- | --- | --- | --- | --- |
| Residue | Ligand | Distance | Residue | Ligand | Distance |
| Gln-2 | OE1 | 2.37Å | Gly-169 | O | 2.66Å |
| Asp-41 | OD1 | 2.42Å | Tyr-171 | O | 2.97Å |
| Asp-41 | OD2 | 2.52Å | Val-174 | O | 2.66Å |
| Leu-75 | O | 2.29Å | Glu-195 | O | 3.00Å |
| Asn-77 | OD1 | 2.41Å | Asp-197 | OD1 | 2.84Å |
| Ile-79 | O | 2.29Å | Water 1 | O | 2.71Å |
| Val-81 | O | 2.37Å | Water 2 | O | 2.97Å |
| | Mean | 2.39Å | | Mean | 2.89Å |

*Ligand is defined as those atoms that are in the first coordination sphere of the metal ion, and which have formal negative or partial negative charges.

The chemical properties of these two sides are as different as their structures might suggest. For example, a single crystal of wild type subtilisin was soaked for 24 hours in 5 mM EDTA near 4° C. and diffraction data was collected to 2.0Å resolution. Difference Fourier [F(native-F(EDTA)] analysis revealed that no change had occurred at site A. This result is consistent with metal ion analysis of the wild type protein after exhaustive dialysis against a 1 mM solution of EDTA (20 mM Hepes) at 4° C. Under these conditions it was found that the protein still bound 0.45 moles of calcium per mole of enzyme. Results similar to this had been reported by Voordouw et al., Biochemistry, 15:3716-37 (1976) who estimated the $K_d$ of calcium binding to subtilisin BPN' to be less than that for EDTA ($K_d$ $10^{-11}$) at 25° C. We have estimated that $K_d$ for calcium binding to this site to be between $10^{-8}$ and $10^{-12}$ near 60° C., as judged by differential scanning calorimetry in the presence of different metal ion chelates.

The chemical properties of the calcium site B are somewhat different. The F(native)-F(EDTA) difference Fourier analysis indicated a rearrangement of the ion environment at site B after treatment of the crystal with 5 mM EDTA. Interpretation of this difference electron density together with observations made with other subtilisin crystal preparations have lead to the suggestion that the calcium ions at Site B can be readily replaced by smaller monovalent cations such as sodium. This replacement is accompanied by a small shift in ion position and a reorganization of solvent about the ion so that the coordination number is reduced from 7 to 5. Binding of other monovalent cations (K+, and Tl+) has also been reported by Drenth et al. Eur. J. Biochem, 26:177-181 (1972).

Evidence for a weak calcium binding site first came from thermal inactivation kinetic experiments conducted as a function of free calcium ion concentration. As the calcium concentration was increased above 0.1 mM, the half-life for the rate of thermal inactivation at 65° C. was observed to increase from about 1 minute to approximately 200 minutes at calcium ion concentrations of 100 mM to 300 mM (see FIG. 4). This data was found to closely fit a theoretical titration curve for a binding site that has a Kd of 32 mM for a single calcium ion. Other Group II metal ions such as $Mg^{2+}$, $Ba^{2+}$, and $Sr^{2+}$ were similarly tested. The former two metal ions were found to be ineffective for the stabilization of subtilisin in this same concentration range as shown in FIG. 4. The $Sr^{2+}$ ions, however, were found to increase the thermal stability of the enzyme but the higher concentration necessary to have an effect suggested a much weaker affinity for this site. The concentration of $SrCl_2$ necessary to give a stabilization equal to that of $CaCl_2$ is about 20 times higher, suggesting a Kd for binding of $Sr^{2+}$ to be in the 0.7M range. These results with the Group II metal ions are typical of calcium binding sites in proteins (Stuart et al., Nature 324:84-87 (1986)) and reflects a selectivity based on size preference. The ionic radius of $Mg^{2+}$, 0.78Å (Ladd radius; Cotton & Wilkinson, Advanced Inorganic Chemistry, Interscience, John Wiley, N.Y. 3d ed. (1972)), is apparently too small, and the ionic radius of $Ba^{2+}$, 1.43Å, is apparently too large. The ionic radius of $Sr^{2+}$, 1.27Å, can be accommodated, but the ionic radius of $Ca^{2+}$, 1.06Å, apparently fits the best. A similar result was found by Holguin (Arch. Biochem. Biophys., 251:9-16 (1986)) for purified Ca-ATPase from sarcoplasmic reticulum.

It is also possible to measure the effect of the free calcium ion concentration on the thermal stability of subtilisin BPN' through the use of differential scanning calorimetry (DSC). Increasing the calcium ion concentration above 0.1 mM causes the midpoint for the thermally induced unfolding transition, Tm, to increase from about 69.5° C. for the protein as isolated where it binds 1 mole calcium/mole protein, to approximately 80° C. for the protein in the presence of 150 mM $CaCl_2$.

The next necessary step taken was to correlate the data in FIG. 4 with one of the two structural sites identified by X-ray crystallography. In light of all the available chemical and physical information described above, it was possible to nominate the calcium site B as the most likely candidate responsible for the weak calcium binding demonstrated in FIG. 4 for wild type subtilisin BPN'.

Through the use of the rules outlined above for the selection of the amino acid residues to be altered, a decision was made to change Pro 172 to Asp. Pro 172 is part of one of the loops that comprise the calcium site B. The simulated carboxylate chain is approximately 5Å from the bound metal ion. This particular amino acid residue is somewhat variable in related subtilisin sequences. (It exists as an Asp in subtilisin Carlsberg.) Finally, simulation on a graphics screen showed that it should fit without van der Waals radii violations. The change was introduced by site-directed mutagenesis, essentially as described above and by Bryan et al., Proc. Nat'l Acad. Sci. USA, 83:3743-3745 (1986) (incorporated herein by reference), and the new strain of *B. subtilis* containing the altered subtilisin gene was called GX7172. The variant protein product of that gene was purified and analyzed for enhanced metal ion binding and stability. The results are shown in FIG. 4 and compared with that for the wild type protein (the new protein is labeled 7172).

The calcium ion dependence on the half-life (t1/2) for thermal inactivation of subtilisin 7172 is clearly shifted toward lower calcium ion concentrations. The theoretical titration curve that best approximates the data is one for a single site with $K_d=6$ mM. It therefore appears that changing Pro 172 to Asp increases the affinity of the B site for calcium by about 5-fold over the wild type. The magnitude of this change, $\Delta pK=0.7$, is consistent with theoretical considerations for the introduction of a negative charge at about 5Å from a metal cation given the known difficulties currently associated with the application of electrostatic theory in proteins. Further support for this supposition comes from mutagenesis experiments with staphylococcal nuclease where it was found that changing the Asp 40 carboxylate ligand to Gly caused an 8-fold decrease in calcium binding to the weak calcium site (Kd=1 mM) in this protein (Serpersu et al., *Biochemistry* 26:1289-1300 (1987)). These results therefore provide convincing evidence that the weak calcium binding site measured by thermal inactivation corresponds to the calcium B site identified through X-ray crystallography. Moreover, these results clearly demonstrate the ability to stabilize subtilisin BPN' in the presence of decreasing concentrations of calcium by increasing the metal binding affinity of the site. The extrapolated outcome of continued alteration of site B is the eventual shift in the titration curve so that $K_d$ is so small that no excess metal ion (or dramatically reduced amounts) will be necessary to produce the stability one sees at 100 mM Ca for the wild type protein.

In addition to changing Pro 172 to Asp, Pro 172 was also changed to Glu. The calcium dependence of the rates of thermal inactivation were also examined for this new variant (8312) and the results were found to be almost identical with that of subtilisin 7172.

The amino acids at the calcium A site were also changed to increase thermal stability. In strain 8347, Asn 76 was changed to Asp. In strain 8364, Ser 78 was changed to Asp. In strain 8374, these mutations, Asn 76 to Asp and Ser 78 to Asp, were combined by oligonucleotide-directed mutagenesis. A shown in Table III, the calcium binding affinity of 8374 is increased in an additive fashion over each mutation alone. All three strains showed increased stability over the wild-type (BPN') and over subtilisin Carlsberg.

Furthermore, the changes made in the calcium B binding site may be made in combination with those made in the calcium A binding site in order to increase stability. Thus, for example, the mutation Asn 76 to Asp and Pro 172 to Asp (or Glu) may be made. Additional examples would include Asn 76 to Asp, Ser 78 to Asp, Pro 172 to Asp (or Glu) and Gly 131 to Asp; Asn 76 to Asp and Gly 131 to Asp; Ser 78 to Asp and Gly 131 to Asp: Ser 78 to Asp and Pro 172 to Asp (or Glu); and Ser 78 to Asp, Gly 131 to Asp and pro 172 to Asp (or Glu).

TABLE III

| Enzyme | Stability in Citrate-based Detergents at 37° C. | |
|---|---|---|
| (hr) | Changes | Half-Life |
| Wild-type (BPN') | — | 7 |
| GX 8347 | Asn 76 to Asp | 30 |
| GX 8364 | Ser 78 to Asp | 24 |
| GX 8374 | Asn 76 to Asp and Ser 78 to Asp | ~80 |
| Subtilisin Carlsberg | 82 changes | 12 |

EXAMPLE II

Insertions and/or Deletions of Amino Acid Residues

In addition to substitution of amino acid residues, insertions and/or deletions of amino acid residues in the vicinity of the binding site of interest can be done in a further attempt to influence the electrostatic forces at that site. This can be thought of as a method for optimizing the distance and geometry of ligand interactions. For example, an insertion between residue 172 and 173 in one of the loops that comprises the calcium B site in subtilisin 7172 may be effected in order to move the Asp at residue 172 closer to the bound metal so that it may become a formal ligand and possibly displace one of the bound water molecules.

In searching the Brookhaven Protein Data Bank for peptide sequences the conformational structure of which match parts of the subtilisin BPN' from residue 168 to residue 175, several sequences were found which matched well at residues 170-171 and at residues 173-174, but which had one extra amino acid residue inserted. All of these peptides had the main chain deformed in a way that would permit the side chain of residue 172 to tip more toward the calcium binding site. The carbonyl oxygens which bind to calcium were not significantly disturbed in this computer simulation. If the residue inserted happens to be an Asp or a Glu then one would gain another opportunity for further influencing the electrostatic interaction at this site.

An amino acid deletion may also cause a more favorable environment for metal ion binding by altering the intercharge distance and geometry of neighboring residues.

EXAMPLE III

Enhancing Stability Using Random Mutagenesis

The 7142 variant of subtilisin was generated and identified by a method of random mutagenesis which exposed the entire subtilisin gene to mutagenic agents. (See U.S. patent application Ser. No. 828,545 and PCT Application PCT/US87/00348.) In this particular case the mutagenic agent was sodium bisulfite and the filter assay identified this protein as a stable mutant. DNA sequencing revealed that subtilisin 7142 had two amino acid changes: Gly 131 to Asp, and Ala 116 to Thr. These changes were then introduced individually by site-directed mutagenesis in order to investigate the physical properties of the individual amino acid substitutions. The Gly 131 to Asp change alone was found to be solely responsible for the observed stabilization. This new variant was designated subtilisin 7148. The Ala 116 to Thr change was found to have no effect on the rate of thermal inactivation. By changing Gly 131 to Glu, the results on calcium dependence of the rates of thermal inactivation may be similar with the amino acid substitution to Asp.

When subtilisin 7148 was analyzed for kinetic stability as a function of the calcium ion concentration it was found to have a slightly increased affinity for calcium ions as shown in FIG. 5. In this case, the data was found to be best approximated by a theoretical titration curve for a single binding site with a Kd of 15 mM. This apparent 2-fold increase in metal ion affinity, or $\Delta pK = 0.33$, correlates very well with X-ray crystallography data on subtilisin 7142. The 1.8Å resolution crystal structure for subtilisin 7142 shows the carboxylate group of the new Asp 131 residue to be approximately 10Å from the metal ion at the calcium B site. Therefore the magnitude of the observed increase in metal ion affinity is about what one would expect in light of this intercharge distance. For example, Thomas et al., *Nature* 318:375-376 (1985), observed a 0.29+0.04 shift in the pKa of His 64 of subtilisin BPN' after changing Asp 99 to Ser which is 14Å away. Moreover, if the introduction of a negatively charged residue 5Å away from the metal ion bound at the calcium B site causes a $\Delta pK = 0.7$, then it is entirely consistent with the theory (equation 1) that the introduction of a negatively charged group at 10Å from the site gives a $\Delta pK = 0.33$.

The mutations Gly 131 to Asp and Pro 172 to Asp were combined by oligonucleotide-directed mutagenesis to create strain 8331. The calcium binding affinity of 8331 is increased in an additive fashion.

Regional-directed in vitro random mutagenesis can be used to alter subtilisin BPN' for enhanced thermal stability. In this particular application of random mutagenesis only that part of the subtilisin gene that codes for amino acid residues in the loops responsible for metal ion binding is subjected to mutagenesis. The methods used for random mutagenesis are those described in U.S. patent application Ser. No. 828,545 and PCT application PCT/US87/00348, both incorporated herein by reference.

In the subtilisin BPN', the calcium B site is comprised of only two short stretches of polypeptide chain (residues 169-174 and 195-197). Because of this, it is relatively convenient to specifically target this region for in vitro random mutagenesis. This was accomplished by creating recognition sites for restriction endonucleases in the cloned subtilisin gene at sequence flanking the two target areas. For example, to target the residues 169 to 174 loop of the B-site, oligonucleotide-directed mutagenesis was used to create an XhoI cutting site at residue 162 and a BglI site at residue 176. By taking advantage of the redundancy of the genetic code, these restriction sites were introduced without altering the amino acid sequence specified by the gene. Random mutations were created in the target region by cleaving the gene with XhoI and BglI and then ligating synthetic DNA fragments into the gap created in the gene by the two restriction enzymes. The DNA fragments were synthesized in such a manner that changes from the native DNA sequence occurred at random. Using this procedure, the synthesis of the DNA insert can be controlled so that mutations occur at any frequency, from very minor variation from the native sequence to a completely random sequence.

Although the foregoing invention has been described in some detail by way of illustration and example for purposes of clarity and understanding, it will be obvious that certain changes and modifications may be practiced within the scope of the invention, as limited only by the scope of the appended claims.

What is claimed is:

1. A variant subtilisin with increased thermal stability over the corresponding wild-type subtilisin, wherein said variant subtilisin is obtained by altering the amino acid sequence at a calcium ion binding side such that the electrostatic attractive interaction between the amino acids at said calcium ion binding site and a calcium ion is increased relative to that of said corresponding wild-type subtilisin.

2. The variant subtilisin of claim 1 wherein said wild-type subtilisin is selected from the group consisting of subtilisin BPN', subtilisin Carlsberg, subtilisin DY, subtilisin amylosacharitricus, and mesentericopeptidase.

3. The variant subtilisin of claim 2 wherein the calcium A binding side is altered to increase thermal stability.

4. The variant subtilisin of claim 2 wherein both the calcium A binding site and the calcium B binding site are altered to increase thermal stability.

5. A thermally stable variant subtilisin with increased thermal stability over its corresponding wild-type subtilisin wherein said variant subtilisin has one or more amino acid substitutions selected from the group consisting of Gly 131 to Asp, and Pro 172 to Asp or to Glu.

6. A thermally stable variant subtilisin with increased thermal stability over its corresponding wild-type subtilisin, wherein said variant subtilisin comprises an amino acid substitution of Pro 172 to Asp.

7. A thermally stable variant subtilisin with increased thermal stability over its corresponding wild-type subtilisin, wherein said variant subtilisin comprises an amino acid substitution of Gly 131 to Asp.

8. A thermally stable variant subtilisin with increased thermal stability over its corresponding wild-type subtilisin, wherein said variant subtilisin comprises an amino acid substitution of Pro 172 to Glu.

9. A thermally stable variant subtilisin with increased thermal stability over its corresponding wild-type subtilisin, wherein said variant subtilisin comprises an amino acid substitution of Gly 131 to Asp and Pro 172 to Asp.

10. A washing preparation comprising the variant subtilisin of any one of claims 2-9.

11. A method for improving the removal of proteinaceous stains on fabric comprising contacting said fabric with the washing preparation of claim 10 and cleaning said stained fabric with said washing preparation.

* * * * *

UNITED STATES PATENT AND TRADEMARK OFFICE
CERTIFICATE OF CORRECTION

PATENT NO. : 5,260,207

DATED : November 9, 1993

INVENTOR(S) : PANTOLIANO, M.W. et al.

It is certified that error appears in the above-indentified patent and that said Letters Patent is hereby corrected as shown below:

Figure 1: amend the formal drawing to note where the "CaB" site is and where the "DFP" site is.

delete

FIG. 1 and replace therein

FIG. 1

UNITED STATES PATENT AND TRADEMARK OFFICE
CERTIFICATE OF CORRECTION

PATENT NO. : 5,260,207

DATED : November 9, 1993

INVENTOR(S) : PANTOLIANO, M.W. et al.

It is certified that error appears in the above-indentified patent and that said Letters Patent is hereby corrected as shown below:

Title page, line 4 in item [75] "Inventors," after "Md." add --Robert C. Ladner, Ijamsville, MD--.
Column 1, line 10 in the section entitled "Other Publications, delete "Birchem." and insert therein --Biochem.--.
Column 3, line 41, between the two parentheses, insert --▲--; line 42, between the two parentheses that are after the word "by", insert --■--; line 42, between the two parentheses that are after the word "The", insert --●--.
Column 4, line 9, (Table 1, column 2: the Glutamic acid line), delete "Gly" and replace therein --Glu--.
Column 8, line 54, after "from" insert --*Bacillus* species such as subtilisin BPN' from--; line 64, delete "o" and insert therein --of--.
Column 11, line 45, after "native" insert --)--; line 45, after "EDTA" insert --)--.
Column 13, last line, delete "pro" and insert therein --Pro--.
Delete claim 5; delete claim 7.

Signed and Sealed this

Eighth Day of July, 1997

Attest:

BRUCE LEHMAN

Attesting Officer

Commissioner of Patents and Trademarks

UNITED STATES PATENT AND TRADEMARK OFFICE
CERTIFICATE OF CORRECTION

PATENT NO. : 5,260,207

DATED : November 9, 1993

INVENTOR(S) : PANTOLIANO, M.W. et al.

It is certified that error appears in the above-indentified patent and that said Letters Patent is hereby corrected as shown below:

Column 16, line 4 in claim 1, delete "side" and insert therein --site--; delete claim 5; delete claim 7.

Signed and Sealed this

Twenty-ninth Day of July, 1997

Attest:

BRUCE LEHMAN

Attesting Officer

Commissioner of Patents and Trademarks